United States Patent
Aarts et al.

(10) Patent No.: US 8,879,746 B2
(45) Date of Patent: Nov. 4, 2014

(54) METHOD AND DEVICE FOR REDUCING SNORE ANNOYANCES

(75) Inventors: Ronaldus Maria Aarts, Geldrop (NL); Felix Henric Govert Ogg, Eindhoven (NL); Privender Kaur Saini, Veldhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 368 days.

(21) Appl. No.: 13/266,246

(22) PCT Filed: Apr. 23, 2010

(86) PCT No.: PCT/IB2010/051786
§ 371 (c)(1),
(2), (4) Date: Oct. 26, 2011

(87) PCT Pub. No.: WO2010/125507
PCT Pub. Date: Nov. 4, 2010

(65) Prior Publication Data
US 2012/0045071 A1    Feb. 23, 2012

(30) Foreign Application Priority Data

Apr. 28, 2009    (EP) .................................. 09158902

(51) Int. Cl.
| A61F 11/06 | (2006.01) |
| A61F 5/56 | (2006.01) |
| G10K 11/175 | (2006.01) |
| H04B 15/00 | (2006.01) |

(52) U.S. Cl.
CPC ............... *G10K 11/175* (2013.01); *A61F 5/56* (2013.01)
USPC ......................................... 381/71.1; 381/94.1

(58) Field of Classification Search
CPC ...... A61B 5/4818; A61B 5/7275; A61B 1/24; A61B 5/113; A61B 7/003
USPC ......... 381/73.1, 71.1–71.8, 57, 92, 94.1, 122; 600/545; 128/848
See application file for complete search history.

(56) References Cited

U.S. PATENT DOCUMENTS

| 4,438,526 A | 3/1984 | Thomalla |
| 5,444,786 A * | 8/1995 | Raviv .......................... 381/71.14 |

(Continued)

FOREIGN PATENT DOCUMENTS

| DE | 102004031657 A1 | 2/2006 |
| DE | 102004052845 A1 | 5/2006 |

OTHER PUBLICATIONS

Chakravarthy et al: "Application of Active Noise Control for Reducing Snore"; 2006 IEEE International Conference on Acoustics, Speech and Signal Processing; May 2006, pp. V-305-V-308.

(Continued)

*Primary Examiner* — Vivian Chin
*Assistant Examiner* — Ammar Hamid

(57) ABSTRACT

A method and a device for reducing snore annoyances include determining a snore sound pattern of a snoring person to predict an upcoming snore sound level. A faked snore sound is played to flatten the resulting snore sound level.

13 Claims, 2 Drawing Sheets

(56) References Cited

U.S. PATENT DOCUMENTS

| | | | |
|---|---|---|---|
| 5,781,640 A | | 7/1998 | Nicolino, Jr. |
| 5,844,996 A | | 12/1998 | Enzmann et al. |
| 5,989,193 A | * | 11/1999 | Sullivan .................. 600/534 |
| 7,676,276 B2 | * | 3/2010 | Karell ...................... 607/135 |
| 7,853,024 B2 | * | 12/2010 | Slapak et al. ............ 381/71.1 |
| 2007/0076896 A1 | | 4/2007 | Hosaka et al. |

OTHER PUBLICATIONS

Schafer et al: "Digital Signal Analysis of Snoring Sounds in Children"; International Journal of Pediatric Otorhinolaryngology, vol. 20, 1990, pp. 193-202.

* cited by examiner

METHOD AND DEVICE FOR REDUCING SNORE ANNOYANCES

FIELD OF THE INVENTION

The present invention relates to the field of reducing snore annoyances.

BACKGROUND OF THE INVENTION

It is well-known that the sound produced by a snoring person can be a great annoyance both to the snoring person as well as to a bed-partner of the snoring person. The snoring sound is characterized by periodic loud noise bursts with silent periods in between. Particularly, the partner of a snoring person is woken up many times during the night, by suchlike non-regular snoring sound. Partners wake up specifically when the noise level increases suddenly, but equally so when the snorting stops for a while.

An active noise reduction merely for reducing, using reference signal supply means, an error microphone and control speaker, the level of a noise source, such as an unsteady sound having a varying sound pressure level, an intermittent sound including silent portions and emitted by a sound source that intermittently stops, is disclosed by the document US 2007/076 896 A1, wherein an active noise reduction control apparatus is used to reduce a to-be-reduced noise emitted from the sound source by determining a reference signal in dependency of the noise and generating a control sound which is dephased relatively to the reference signal. An error microphone detects the synthesis of the sound pressure of the control sound and the to-be-reduced noise and if necessary updates filter coefficients of the filtering processing device of the active noise reduction control apparatus. Disadvantageously this active noise reduction control apparatus comprises a comparatively high computing power for processing the very complex and extensive algorithm for reducing the to-be-reduced noise.

SUMMARY OF THE INVENTION

It is an object of the present invention to reduce the snore annoyances caused by non-regular snoring sound by creating a regular, monotonous snoring sound and that does not have the drawbacks mentioned in connection with the prior art.

The above mentioned object is accomplished by a method for reducing snore annoyances comprising the steps of:
  determining a snore sound pattern of a snoring person,
  predicting the upcoming snore sound level in dependency of the determined snore sound pattern and
  playing a faked snore sound to flatten the resulting snore sound level.

The present invention proposes a method that tracks the snoring sounds and produces background noise during the silent periods between the snores. Beneficially, the gaps in the snore sound pattern, which comprise abruptly falling and essentially lower snore sound levels in each case, are filled up with the faked snore sound, so that the synthesis of the snore sound of the snoring person and the faked snore sound provides a regular and monotonous resulting snoring sound. Consequently, the snoring person and the partner of the snoring person are not periodically disturbed by suddenly changing snore sound levels and therefore get a highly better rest and a more comfortable sleep. To avoid constructive interference between the snore sound and the faked snore sound, the snore sound pattern of the snoring person is determined and analyzed to derive the upcoming snore sound level from the snore sound pattern. If an upcoming silent period between the snores is identified, the playback of the faked snore sound starts. The determination of the snore sound pattern particularly comprises a step of extracting an average snore frequency of the snore sound pattern. The faked snore sound preferably features the same sound characteristics as the snore sound of the snoring person. The method preferably uses a microphone, placed in the vicinity of the snorer that records the snoring sounds. Particularly the microphone filters the snore sound for typical snoring sound patterns, disregarding any other noises. The time intervals the snorer is quiet, during breathing in or not snoring at all for instance, is tracked and a frequency fitted snore recording at dimmed volume, for example from a loudspeaker alongside the bed-partner or from ear-plugs worn by the bed-partner, is played. Irregular snoring sounds are thus complemented with snoring echoes making it easy for the partner to blend snores and silent periods. Alternatively, the wording predicting the upcoming snore level in the sense of the present invention could also comprise a reactive step of said method, whereby the actual snore sound level is monitored and the faked snore sound is played, if the monitored snore sound falls below a certain threshold, for instance.

In a preferred embodiment of the present invention a typical snore sound of the snoring person is recorded and used as the faked snore sound. Consequently, the sound characteristics and even the tone colour of the resulting snore sound level are comparatively homogenous.

In another preferred embodiment of the present invention the method comprises a step of extracting a single period interval in the snore sound. The snore sound consists of a time-dependant sequence of multiple similar single period intervals with higher snore sound level. Between these single period intervals the snoring level is significantly lower or at least zero. Therefore, the step of determining the snore sound pattern particularly comprises the step of identifying at least one of these single period intervals and the time lag between two subsequent single period intervals. Preferably, an average single period interval and an average time lag are determined. On the basis of the determined single period interval and the determined time lag an accurate forecast of the upcoming snore sound level can be accomplished in a quite simple manner and in contrast to the state of the art without the usage of high computing power and/or complex algorithm.

Preferably, the accuracy of the single period interval and respectively the time lag between two subsequent single period intervals are increased permanently by continuously analyzing the current snore sound pattern. Particularly, the single period intervals and respectively the average single period interval for a certain user can be stored. Consequently, the accuracy of the predicting of the upcoming snore sound level increases according to the frequency of use. In other words, the method according to the present inventions preferably involves a self-learning progress to increase the quality of reducing snore annoyances. If the snoring pattern changes fundamentally, because of a movement of the snoring person for instance, the former recent single period interval gets rejected and a new single period interval is extracted from the actual snore sound pattern.

In another preferred embodiment of the present invention the step of determining the snore sound pattern includes a step of comparing the determined snore sound pattern with a stored snore pattern. Preferably, the snoring person can be identified by comparing the determined snore sound pattern with a stored sound pattern which is connected to a certain user. Consequently certain snore sound characteristics of this user can be taken into account during the step of predicting the upcoming snore sound level. The stored sound pattern comprises a former determined sound pattern which has been stored in a non-volatile memory unit. Thus, the step of analyzing the snore sound pattern during a starting procedure of the method can be saved.

In another preferred embodiment of the present invention the faked snore sound is smoothly faded out when the snoring of the snoring person stops and/or the faked snore sound comprises a reduced snore sound level relatively to the snore sound pattern.

In another preferred embodiment the resulting snore sound level is additionally reduced by an active noise control mechanism, wherein the active noise control mechanism comprises the step of generating a further sound pattern which is essentially equal to the snore sound pattern and/or the resulting snore sound level and/or which is dephased compared to the snore sound pattern and/or to the resulting snore sound level. The active noise control mechanism generates a further sound pattern which reduces the snore sound pattern by destructive interference. For the efficiency of the active noise control mechanism a very precise analysis of the snore sound pattern or the resulting snore sound level is necessary. The more regular and monotonously the input sound pattern of the active noise control mechanism the more simple, precise and efficient the noise reducing. Consequently, the efficiency of the active noise control mechanism is highly increased by integrating the active noise control mechanism in the method as described above. Preferably, the above mentioned method is used to flatten the snore sound level, whereby the active noise control reduces the resulting snore sound level. Preferably, this leads to a more regular and homogenous error feedback signal of the active noise control mechanism which can simply be processed to adapt the active noise control mechanism.

In another preferred embodiment of the present invention the sound level of the snore sound pattern is reduced by a mandibularly repositioning mechanism accomplished by a mandibularly repositioning device which is inserted into the mouth of the snoring person. Mandibulary repositioning devices in common are used in the clinical setting to reduce snoring. They are inserted into the mouth, to be worn during sleep. An opening between the frontal teeth is designed to provide a free air-flow to breathe through. Beneficially, the usage of the mandibularly repositioning device leads to a lower absolute volume of the snore sound level. Consequently, a comparatively lower faked snore sound has to be generated to flatten the resulting snore sound level and the resulting snore sound level is decreased.

Preferably, the sound level is reduced by sound dispersing means, which are attached to the mandibularly reposition device. The mandibularly repositioning mechanism respectively comprises a step of separating the airflow through the mouth and/or nose of the snoring person into an out-flow and an in-flow, whereby merely the out-flow is guided through the sound dispersing means to reduce the snoring sound of the snoring person. The snore sound level is reduced by using a mandibularly device, equipped with a valve, for instance, that separates out-flow from in-flow. Air flowing inward is not obstructed, but air flowing outward is passed through the sound dispersing material, which mutes the snoring sound. Beneficially, this silences the out-flow snoring noise, harming nor the snorer nor his oxygen supply.

In another embodiment of the present invention the mandibularly repositioning mechanism comprises a step of inducing a spasm of a tongue muscle of the snoring person, whereby respectively a step of tracking the tongue's position and inducing the spasm when the tongue reaches a snoring position is provided. Beneficially, the mandibulary repositioning mechanism comprises a step of inducing a (modest) spasm of the tongue muscle of the snorer, making the person reposition his tongue to a position that does not cause snoring (and the noises). Therefore, the mandibularly repositioning device preferably features electrodes to create such spasms. Preferably, the mandibularly repositioning mechanism comprises a positioning device to track the tongue's position and inflict the mild electric shock when the tongue sinks into "snoring-position".

Another object of the present invention is a device for reducing snore annoyances comprising:
  a microphone for recording a snore sound of a snoring person,
  a processing unit for analyzing just the amplitude of the snore sound and
  a loudspeaker triggered by the processing unit for playing back a faked snore sound.

Beneficially, a device for reducing snore annoyances is provided which is comparatively effective, cost-efficiency and easy to implement, because this device requires significantly less computing and processing power compared to known active noise control mechanism. It is highly disadvantageous that these known active noise control mechanism has to analyze the very complex sound particle velocity of the incoming noise to cancel it by destructive interference. The sound particle velocity comprises high-frequency and partly directional parameters like the phase, the direction and the amplitude of the noise which are altogether very difficult to analyze, particularly in real-time conditions. In contrary, the processing unit of the device according to the present inventions just has to analyze the amplitude of the snore sound as only a constructive interference between the snore sound and the faked snore sound is intended. The amplitude of the snore sound is a scalar and therefore very simple to analyze. In a preferred embodiment this device further comprises an active noise control mechanism with an adaptive filter unit. The faked snore sound is supplied to the entrance and/or to the output of the adaptive filter unit increasing the efficiency of the active noise control mechanism by making the incoming snore sound and/or the resulting snore sound more regular and monotonously. This causes a more regular, homogenous and easier to analyze sound particle velocity and therefore are more homogenous error feedback signal of the active noise control mechanism which can simpler be processed adapting the active noise control mechanism to the resulting snore sound.

Particularly, the method and the device of reducing snore annoyances according to the present invention can also be used to reduce noise annoyances concerning baby crying noise, teeth grinding noise and/or noise from any other intermittent noise source.

These and other characteristics, features and advantages of the present invention will become apparent from the following detailed description, taken in conjunction with the accompanying drawing, which illustrates, by way of example, the principles of the invention. The description is given for the sake of example only, without limiting the scope of the invention. The reference figures quoted below refer to the attached drawing.

DETAILED DESCRIPTION OF EMBODIMENTS

Figure 1:
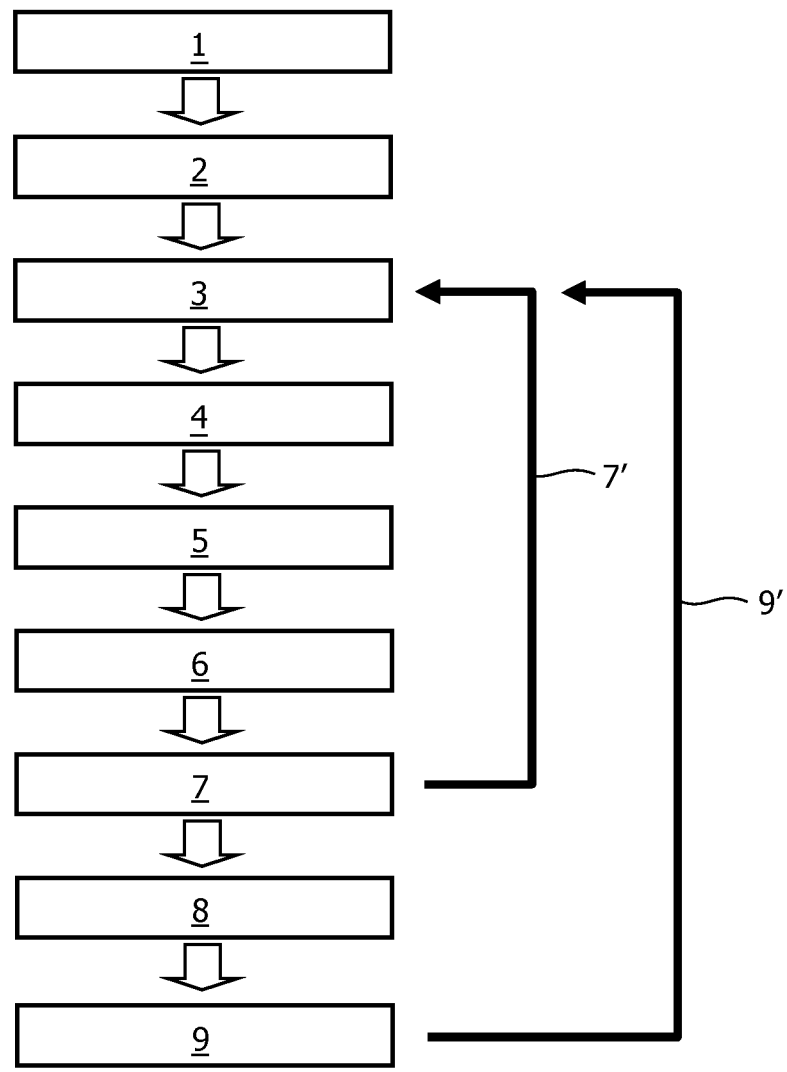
FIG. 1 shows a method for reducing snore annoyances according to a first embodiment of the present invention.

The present invention will be described with respect to particular embodiments and with reference to a certain drawing but the invention is not limited thereto but only by the claims. The drawing described is only schematic and is non-limiting. In the drawing, the size of some of the elements may be exaggerated and not drawn on scale for illustrative purposes.

Where an indefinite or definite article is used when referring to a singular noun, e.g. "a", "an", "the", this includes a plural of that noun unless something else is specifically stated. Furthermore, the terms first, second, third and the like in the description and in the claims are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein. Moreover, the terms top, bottom, over, under and the like in the description and the claims are used for descriptive purposes and not necessarily for describing relative positions. It is to be understood that the terms so used are interchangeable under appropriate circumstances and that the embodiments of the invention described herein are capable of operation in other orientations than described or illustrated herein. It is to be noticed that the term "comprising", used in the present description and claims, should not be interpreted as being restricted to the means listed thereafter; it does not exclude other elements or steps. Thus, the scope of the expression "a device comprising means A and B" should not be limited to devices consisting only of components A and B. It means that with respect to the present invention, the only relevant components of the device are A and B.

FIG. 1 shows a method 10 for reducing snore annoyances according to a first embodiment of the present invention. In a first step 1 the system is turned on and bed partners go to sleep, for instance. During the subsequent second step 2 breathing sounds, talking and the like are not recognized as repetitive sound, hence no playback is generated. In a third step 3 the snoring sound of a partner snoring is recognized with the known snoring patterns stored in a pattern library onboard the device. In a fourth step 4 the system records the snore pattern and extracts a single period interval of snore sounds. Furthermore, the time lag between the single period intervals is derived from the snore sound pattern. In a fifth step 5 the system then predicts the snore sound level of the snorer, according to the pattern the snoring persons is expected to follow. If the snorer does not snore at some moment the snore sound pattern would predict him to, the system plays the single period interval recording in a sixth step 6, to match the predicted pattern. In the seventh step the system keeps monitoring the pattern of snoring, if the snorer does snore. If the pattern changes the system goes back to the third step 7'. In the eights step 8 the system plays a faked snore sound between the single period interval to compensate the snorer's quietness and to flatten the resulting snore sound level. Preferably, the volume of the playout is decreased somewhat. In the ninth step 9 the playback of the faked snore sound is faded out, in case the snoring stops. If the snoring starts again, the system goes back to the third step 9'.

Figure 2:
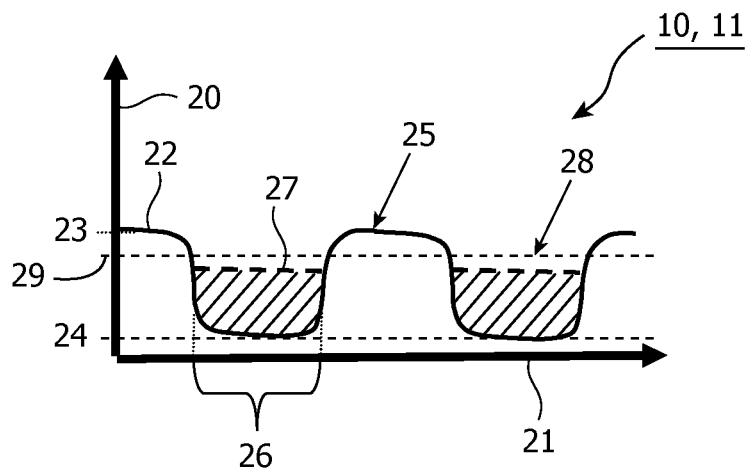
FIG. 2 shows a the resulting noise level of a method for reducing snore annoyances according to the first embodiment of the present invention.

In FIG. 2 the resulting noise level of a method 10 for reducing snore annoyances according to the first embodiment of the present invention is shown. The noise level 20 is shown on the x-axis and the time 21 on the y-axis of the illustrated diagram. The snore sound level 22 strongly deviates with time 21 between a maximum noise level 23 and a minimum noise level 24. For a length of a time leg 26 between the single period intervals 25 the snore sound level 22 sinks on the minimum noise level 24. The method according to the present invention detects the snore sound pattern and predicts the upcoming snore sound level in dependency of the determined snore sound pattern. A faked snore sound 27 is played during the time legs 22 and fills up the gaps 28 in the snore sound pattern when the snore sound level 22 sinks on the minimum noise level 24. Consequently, the resulting snore 29 sound comprising the snore sound level 22 and the faked snore sound 27 shows a comparatively regular and monotonous sound level.

Figure 3:
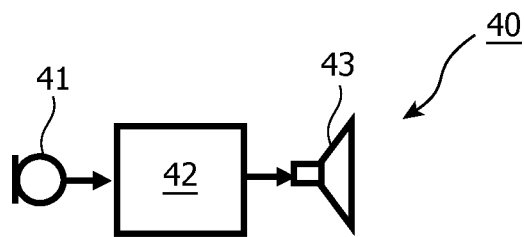
FIG. 3 shows a device for reducing snore annoyances according to a first embodiment of the present invention and FIG. 4 shows a device for reducing snore annoyances according to a second embodiment of the present invention.

In FIG. 3 a device 40 for reducing snore annoyances according to a first embodiment of the present inventions is shown, wherein the device 40 performs the method 10 for reducing snore annoyances according to the first embodiment of the present invention explained in FIGS. 1 and 2. For that purpose, the device 40 comprises a microphone 41 for recording the snore sound of the snoring person, a processing unit 42 for determining the snore sound pattern 11 in the snore sound of the snoring person and for predicting the upcoming snore sound level 22 in dependency of the determined snore sound pattern 11 and a loudspeaker 43 for playing back a faked snore sound 27 to flatten the sound level 20 of the resulting snore sound 29. The gaps 28 in the snore sound pattern are filled up with the faked snore sound 27 to provide a more regular and homogenous resulting snore sound 29.

Figure 4:
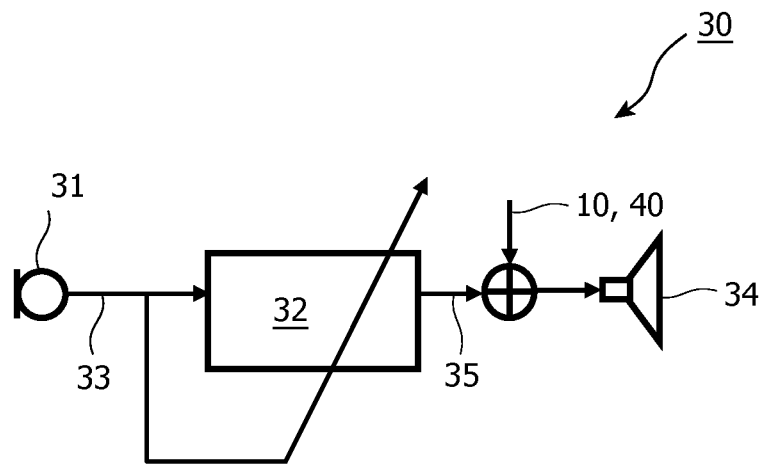

FIG. 4 shows a device for reducing snore annoyances according to a second embodiment of the present invention, wherein the second embodiment is a combination of the first embodiment illustrated in FIG. 3 and an active noise control mechanism 30 (ANC). The active noise control mechanism 30 comprises a further microphone 31 recording the resulting snoring sound, an adaptive filter unit 32 filtering the recorded snoring sound signal 33 and a further loudspeaker 34 for playing an output sound in according with an output signal 35 from the adaptive filter unit 32. The filter coefficients of the filter unit 32 are adapted in dependency of the recorded snoring sound signal 33 to minimize the resulting snoring sound comprising the snoring sound pattern and the output sound. Furthermore, the gaps 28 in the snore sound pattern are filled up with the faked snore sound 27 by integrating the method 10, the device 40 and/or the processing unit 42 of a device 40 for reducing snore annoyances according to the first embodiment of the present invention, described in FIGS. 1 and 3, in the pathway between the further loudspeaker 34 and the adaptive filter unit 32. The more regular and monotonously the resulting input sound of the active noise control mechanism 30 the more simple, precise and efficient works the active noise control mechanism 30. Consequently, the integration of an active noise control mechanism 30 in the method 10 for reducing snore annoyances according to the first embodiment of the present invention provides a comparatively accurate method both for flattening and for reducing the resulting snore sound level. The place of the addition of the method 10 for reducing snore annoyances according to the first embodiment of the present invention is not restricted to the one shown in FIG. 3 but it can be at the entrance of the adaptive filter as well.

The invention claimed is:

1. A method for reducing snore annoyances comprising acts of: determining a snore sound pattern in a snore sound of a snoring person; predicting an upcoming snore sound level in dependency of the determined snore sound pattern; and playing a faked snore sound to flatten a sound level of a resulting snore sound of a combined sound including the snore sound and the faked snore sound, wherein the determining act includes an act of extracting snore intervals in the snore sound of the snoring person, and wherein the playing plays the faked snore sound at least partly fill up gaps in the sound level between the snore intervals.

2. The method according to claim 1, wherein the determining act includes an act of comparing the determined snore sound pattern with a stored former snore sound pattern to identify the snoring person.

3. The method according to claim 1, wherein accuracy of the intervals is continuously adapted by analyzing a current snore sound of the snoring person.

4. The method according to claim 1, wherein the faked snore sound comprises a reduced snore sound level relatively to the snore sound pattern.

5. The method according to claim 1, wherein the faked snore sound is faded out when the snore sound stops.

6. The method according to claim 1, further comprising an act of recording the snore sound of the snoring person wherein the playing act plays back the recorded snore sound.

7. The method according to claim 1, further comprising an act of reducing a resulting snore sound level of the resulting snore sound by an active noise control mechanism, wherein the reducing act comprises an act of generating a further sound pattern which is essentially equal to the snore sound pattern and/or to the resulting snore sound level and/or which is dephased and compared to the snore sound pattern and/or to the resulting snore sound level.

8. The method according to claim 1, further comprising an act of reducing the sound level by a mandibularly repositioning mechanism accomplished by a mandibularly repositioning device which is inserted into the mouth of the snoring person.

9. The method according to claim 8, wherein the sound level is reduced by a sound disperser, which is attached to the mandibularly reposition device, wherein the mandibularly repositioning mechanism is configured to separate the airflow through the mouth and/or nose of the snoring person into an out-flow and an in-flow, wherein the out-flow is guided through the sound disperser.

10. The method according to claim 8, wherein the mandibularly repositioning mechanism is configured to induce a spasm of a tongue muscle of the snoring person and/or track the tongue's position and induce the spasm when the tongue reaches a snoring position.

11. A device for reducing snore annoyances comprising:
a microphone for recording a snore sound of a snoring person including snore intervals of snore levels separated by gaps of sound levels less than the snore levels;
a processor configured to analyze the snore levels occurring during the snore intervals separated by the gaps; and
a loudspeaker triggered by the processor for playing a faked snore sound, wherein the faked snore sound is played during the gaps.

12. The device according to claim 11, further comprising an active noise control mechanism, wherein the active noise control mechanism comprises an adaptive filter unit, wherein the processor is connected to an input and/or to the output of the adaptive filter unit.

13. A method for reducing snore annoyances comprising acts of: determining a snore sound pattern in a snore sound of a snoring person, wherein the determining act includes an act of extracting single period intervals in the snore sound of the snoring person including a snore sound level, averaging the extracted single period intervals, and storing an average single period interval, the single period intervals being separated by gaps devoid of the snore sound level; predicting an upcoming snore sound level based on the determined snore sound pattern and the average single period interval; and playing a faked snore sound to flatten a sound level of a resulting snore sound, wherein the playing act plays the faked snore sound during the gaps.

* * * * *